(12) United States Patent
DeLuca et al.

(10) Patent No.: US 10,105,375 B2
(45) Date of Patent: Oct. 23, 2018

(54) COMBINATION OF LOW DOSE 2-METHYLENE-19-NOR-(20S)1α, 25-DIHYDROXYVITAMIN $D_3$ AND CALCIMIMETICS TO TREAT SECONDARY HYPERPARATHYROIDISM

(71) Applicant: Wisconsin Alumni Research Foundation, Madison, WI (US)

(72) Inventors: Hector F. DeLuca, Deerfield, WI (US); Margaret Clagett-Dame, Deerfield, WI (US); Lori A. Plum, Arena, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/666,244

(22) Filed: Aug. 1, 2017

(65) Prior Publication Data
US 2018/0055856 A1 Mar. 1, 2018

Related U.S. Application Data

(60) Provisional application No. 62/381,372, filed on Aug. 30, 2016, provisional application No. 62/422,425, filed on Nov. 15, 2016.

(51) Int. Cl.
| | | |
|---|---|---|
| A61K 31/593 | (2006.01) |
| A61K 31/137 | (2006.01) |
| A61K 38/08 | (2006.01) |
| A61K 9/00 | (2006.01) |
| A61K 47/10 | (2017.01) |
| A61K 9/08 | (2006.01) |
| A61K 47/44 | (2017.01) |

(52) U.S. Cl.
CPC .......... *A61K 31/593* (2013.01); *A61K 9/0019* (2013.01); *A61K 9/0095* (2013.01); *A61K 9/08* (2013.01); *A61K 31/137* (2013.01); *A61K 38/08* (2013.01); *A61K 47/10* (2013.01); *A61K 47/44* (2013.01)

(58) Field of Classification Search
CPC .................................................. A61K 31/4747
See application file for complete search history.

(56) References Cited

U.S. PATENT DOCUMENTS

| | | |
|---|---|---|
| 5,843,928 A | 12/1998 | DeLuca et al. |
| 9,034,853 B2 | 5/2015 | DeLuca et al. |

(Continued)

FOREIGN PATENT DOCUMENTS

WO 2016109156 A1 7/2016

OTHER PUBLICATIONS

Am. J. of Kidney Diseases, v.39, No. 2, Suppl. 1 (Feb. 2002), pp. 546-575.

(Continued)

*Primary Examiner* — San Ming R Hui
(74) *Attorney, Agent, or Firm* — Andrus Intellectual Property Law, LLP

(57) ABSTRACT

Disclosed are pharmaceutical compositions and methods of combination therapy that include or utilize low doses of 2-methylene-19-nor-(20S)-1α,25-dihydroxyvitamin $D_3$ and a calcimimetic to treat and/or prevent secondary hyperparathyroidism and/or its accompanying symptoms in a subject having or at risk for developing secondary hyperparathyroidism.

24 Claims, 4 Drawing Sheets

(56) References Cited

U.S. PATENT DOCUMENTS

| | | | |
|---|---|---|---|
| 2007/0185211 A1* | 8/2007 | Wizel | A61K 31/137 514/649 |
| 2008/0249068 A1* | 10/2008 | DeLuca | A61K 31/565 514/103 |
| 2011/0028394 A1 | 2/2011 | Karim et al. | |
| 2014/0005152 A1 | 1/2014 | DeLuca et al. | |

OTHER PUBLICATIONS

Brown et al., "Selective Vitamin D Analogs and their Therapeutic Applications," Sem. Nephrol 14:156-174, 1994.

Brown et al., "The Non-Calcemic Analog of Vitamin D, 22-oxacalcitriol (OCT) Suppresses Parathyroid Hormone Synthesis and Secretion," J. Clin. Invest. 84:728-732, 1989.

Darwish & DeLuca, "Identification of a transcription factor that binds to the promoter region of the human parathyroid hormone gene," Arch. Biochem. Biophys. 365, 123-130, 1999.

DeLuca, "Vitamin D: The vitamin and the hormone," Fed. Proc. 33, 2211-2219, 1974.

DeLuca & Schnoes, "Vitamin D: Recent advances," Ann. Rev. Biochem. 52, 411-439, 1983.

Demay et al., "Sequences in the human parathyroid hormone gene that bind the 1,25-dihydroxyvitamin D3 receptor and mediate transcriptional repression in response to 1,25-hydroxyvitamin D3." Proc. Natl. Acad. Sci. USA 89, 8097-8101, 1992.

De Schutter et al., Calcif Tissue Int (2012) 91:307-315.

Finch et al., Am J. Physiol Renal Physiol 298:F1315-F1322.

Jung et al., J. Hypertension, vol. 30, No. 11, Nov. 2012, 2182-2191.

Kim, James Wonkee, Effects of calcitriol on the MRL/MpJ-fas/lpr model of systemic lupus erythematosus (Ph.D. Thesis, University of Wisconsin—Madison (2009).

Kumar et al., Drug Metabolism and Disposition, vol. 21, No. 21, 1491-1500.

Miller et al., Nephrol Dial. Transplant (2012) 27:2198-2205.

Shevde et al., "A Potent Analog of $1\alpha$, 25-dihydroxyvitamin D3 Selectively Induces Bone Formation" PNAS, vol. 99, No. 21 pp. 13487-13491 (2002).

Slatopolsky et al., "Marked Suppression of Secondary Hyperparathyroidism by Intravenous Administration of 1,25-dihydroxycholecalciferol in Uremic Subjects," J. Clin. Invest. 74:2136-2143, 1984.

Walter et al., BMC Nephrology 2014, 15:81.

Walter et al., J. Pharmacology and Experimental Therapeutics, 2013, 346:229-240.

Wu-Wong et al., Physiological Reports ISSN 2051-817x, pp. 1-10.

Cozzolino: et al., "Treatment of Secondary Hyperparathyroidism: the clinical utility of etelcalcetide", Therapeutics and Clinical Risk Management (2017) 13, pp. 679-689.

Montenegro, et al., "Efficacy and safety of cinacalcet for the treatment of secondary hyperparathyroidism in patients with advanced chronic kidney disease before initiation of regular dialysis", Nephrology (2012) 17, pp. 26-31.

International Search Report and Written Opinion for PCT/US2017/044922 dated Oct. 20, 2017.

* cited by examiner

COMBINATION OF LOW DOSE 2-METHYLENE-19-NOR-(20S)1α, 25-DIHYDROXYVITAMIN D₃ AND CALCIMIMETICS TO TREAT SECONDARY HYPERPARATHYROIDISM

CROSS-REFERENCE TO RELATED PATENT APPLICATIONS

This patent application claims the benefit of priority under 37 C.F.R. § 1.119(e) to U.S. Provisional Patent Application No. 62/422,425, filed on Nov. 15, 2016, and to U.S. Provisional Patent Application No. 62/381,372, filed on Aug. 30, 2016, the contents of which are incorporated herein by reference in their entireties.

BACKGROUND

This invention relates to vitamin D compounds useful in treating and/or preventing secondary hyperparathyroidism and/or the symptoms thereof, and more particularly to the use of the vitamin D compound 2-methylene-19-nor-(20S)-1α,25-dihydroxyvitamin $D_3$, otherwise referred to herein as "2MD" in combination with calcimimetics to treat and/or prevent secondary hyperparathyroidism and/or the symptoms thereof in subjects having secondary hyperparathyroidism.

Secondary hyperparathyroidism refers to the excessive secretion of parathyroid hormone (PTH) by the parathyroid glands in response to hypocalcemia (low blood calcium levels). This disorder is especially seen in subjects with chronic renal failure and often is abbreviated as "SHPT" in medical literature.

Renal disease has become an increasingly important health problem in virtually every country in the world including highly developed countries such as the United States. Presently there are about 250,000 subjects in the United States on renal dialysis who have lost almost complete use of their kidneys. There are approximately ten times more subjects who have lost some degree of renal function due to renal disease and are progressing to complete renal failure. Renal failure is evidenced by a decreased glomeruli filtration rate (GFR) from a high value of 110 ml/minute/1.73 $m^2$ to 30 ml/minute/1.73 $m^2$ where dialysis is often initiated, and may be referred to as Stage 5, Chronic Kidney Disease (CKD).

Many factors contribute to the development of renal disease. High blood pressure is one of the significant contributors, as is having Type I or Type II diabetes. Current treatments for renal failure are limited to hemodialysis, an extremely expensive procedure that currently is supported by federal governments because individuals typically cannot afford this procedure on their own. The annual cost of renal disease in the United States alone is over $42 billion. Accordingly, effective methods for preventing renal disease and treating symptoms thereof would not only provide a major health benefit but would also provide a major economic benefit.

Secondary hyperparathyroidism (SHPT) has been successfully managed with the use of two types of agents: active vitamin D analogs (AVDs) alone or with the addition of a calcimimetic (CM). Regarding vitamin D's role in managing SHPT, it is now universally accepted that vitamin D must first be 25-hydroxylated in the liver and subsequently 1α-hydroxylated in the kidney before it can be converted to its active form, namely 1α,25-$(OH)_2D_3$ or "calcitriol." (See DeLuca, "Vitamin D: The vitamin and the hormone," Fed. Proc. 33, 2211-2219, 1974; and DeLuca & Schnoes, "Vitamin D: Recent advances," Ann. Rev. Biochem. 52, 411-439, 1983). Calcitriol then stimulates a number of physiological processes including: stimulating the intestine to absorb calcium, stimulating the kidney to reabsorb calcium, stimulating the intestine to absorb phosphate, and stimulating bone to mobilize calcium when signaled by high parathyroid hormone (PTH) levels. These actions result in a rise in plasma calcium and phosphorus levels that bring about the healing of bone lesions such as rickets and osteomalacia and prevent the neurological disorder of hypocalcemic tetany.

Accordingly, SHPT is a universal complication in subjects with chronic renal failure because subjects with chronic renal failure are unable to convert 25-hydroxy-vitamin $D_3$ from the liver to its active form of 1α,25-$(OH)_2D_3$ via 1α-hydroxylation in the kidney. As a result of low levels of circulating 1α,25-$(OH)_2D_3$ in subjects with chronic renal failure, intestinal calcium absorption is minimal which subsequently results in insufficient serum calcium levels. In addition, during chronic renal failure, the failing kidneys do not adequately excrete phosphate. When this happens, insoluble calcium phosphate forms in the body and removes calcium from circulation. Ultimately, low levels of circulating 1α,25-$(OH)_2D_3$ and inadequate phosphate excretion contribute to hypocalcemia and secondary hyperparathyroidism because when the parathyroid glands sense a low level of serum calcium (i.e., hypocalcemia), the parathyroid glands secrete an elevated amount of PTH in order to raise calcium mobilization from bone to raise serum calcium.

In addition to SHPT resulting from renal failure, SHPT also can result from gastrointestinal malabsorption syndromes (e.g., chronic pancreatitis, small bowel disease, and malabsorption-dependent bariatric surgery in which the intestines do not absorb vitamins and minerals properly), where these syndromes are characterized by insufficient absorption of the fat soluble vitamin D resulting in low levels of circulating 1α,25-$(OH)_2D_3$. Other less common causes of secondary hyperparathyroidism are long-term lithium therapy, vitamin D deficiency, malnutrition, vitamin D-resistant rickets, or hypermagnesemia (i.e., abnormally high blood magnesium levels).

As such, overt symptoms of SHPT include increased secretion of PTH. Left unchecked, the elevated secretion of PTH observed in SHPT will lead to the development of renal osteodystrophy. High PTH levels can also lead to: 1) weakening of the bones; 2) calciphylaxis (when calcium forms clumps in the skin and lead to ulcers and potentially death of surrounding tissue); 3) cardiovascular complications; 4) abnormal fat and sugar metabolism; 5) itching (pruritis); and 6) low blood counts (anemia). Less overt symptoms of SHPT include bone and joint pain, bone deformities, broken bones (fractures), swollen joints, kidney stones, increased urination, muscle weakness and pain, nausea, loss of appetite, upper abdominal pain, fatigue, and depression.

Because SHPT results from low levels of circulating calcitriol, calcitriol has been administered as a therapeutic in order to supplement the low levels of circulating calcitriol in subjects with SHPT. In the treatment of SHPT, it is well known that calcitriol binds to the vitamin D receptor (VDR) located in the parathyroid glands to suppress both growth and proliferation of the parathyroid cells and expression of the preproparathyoid gene. (See Demay et al., "Sequences in the human parathyroid hormone gene that bind the 1,25-dihydroxyvitamin $D_3$ receptor and mediate transcriptional repression in response to 1,25-hydroxyvitamin $D_3$." Proc. Natl. Acad. Sci. USA 89, 8097-8101, 1992; and Darwish & DeLuca, "Identification of a transcription factor that binds to the promoter region of the human parathyroid hormone gene," Arch. Biochem. Biophys. 365, 123-130, 1999). Because of its ability to suppress parathyroid hormone (PTH), calcitriol has been used with success in the treatment of secondary hyperparathyroidism. (See Slatopolsky et al., "Marked Suppression of Secondary Hyperparathyroidism by Intravenous Administration of 1,25-dihydroxycholecalciferol in Uremic Subjects," J. Clin. Invest. 74:2136-2143, 1984). However, the use of calcitriol in the treatment of SHPT is not without its drawbacks because calcitriol may cause hypercalcemia resulting from calcitriol's potent action on intestinal calcium absorption and bone mineral calcium mobilization.

As such, less calcemic analogs of calcitriol that exhibit diminished activity on intestinal calcium absorption and/or bone mineral calcium mobilization have been developed and have been found to be nearly as effective as calcitriol in suppressing PTH secretion by cultured bovine parathyroid cells. These include 22-oxacalcitriol (OCT), (Brown et al., "The Non-Calcemic Analog of Vitamin D, 22-oxacalcitriol (OCT) Suppresses Parathyroid Hormone Synthesis and Secretion," J. Clin. Invest. 84:728-732, 1989), as well as 1,25-$(OH)_2$-16-ene-23-yne-$D_3$, 1,25-$(OH)_2$-24-dihomo-$D_3$, and 1,25-$(OH)_2$-24-trihomo-22-ene-$D_3$. 22-oxacalcitriol has been examined in detail for this action in vivo. (See Brown et al., "Selective Vitamin D Analogs and their Therapeutic Applications," Sem. Nephrol 14:156-174, 1994, reporting that 22-oxacalcitriol, despite its rapid clearance in vivo, could suppress PTH mRNA). Low, submaximal doses of calcitriol and OCT exhibited comparable inhibition. OCT also has been shown to suppress serum PTH in uremic rats and dogs.

Another analog of calcitriol with low calcemic and phosphatemic action is 19-nor-1,25-$(OH)_2D_2$, which is also known as paricalcitol or 19-nor-1α,25-dihydroxy-ergocalciferol. Paricalcitol injection is available commercially as Zemplar® from Abbott Laboratories, Abbott Park, Ill. A paricalcitol (Zemplar®) injection is described in U.S. Pat. No. 6,136,799 and has been approved by the FDA and is marketed for the prevention and treatment of secondary hyperparathyroidism associated with chronic renal failure (CKD Stage 5 or end-stage renal disease (ESRD), GFR<15 mL/min/1.73 $m^2$).

A newer class of drug used to treat SHPT are the so-called "calcimimetics," one of which is commercially available as Sensipar® (cinacalcet) in the United States and Australia, and as Mimpara® in the European Union. A calcimimetic (CM) is a drug that mimics the action of calcium on the parathyroid gland by allosteric activation of the calcium-sensing receptor that is expressed in the parathyroid gland. In particular, CMs increase the sensitivity of calcium-sensing receptors in the parathyroid gland and trick the parathyroid gland into thinking that there is a sufficient level of serum calcium. As a result of the receptor thinking that there is sufficient serum calcium, PTH secretion is reduced. (See Miller et al., Nephrol Dial. Transplant (2012) 27:2198-2205; Walter et al., BMC Nephrology 2014, 15:81; Wu-Wong et al., Physiological Reports ISSN 2051-817x, pages 1-10; Kumar et al., Drug Metabolism and Disposition, Vol. 21, No. 21, 1491-1500; and Walter et al., J. Pharmacology and Experimental Therapeutics, 2013, 346:229-240). Calcimimetics have achieved positive responses and are FDA approved for use in subjects on dialysis, but have not been approved for use in chronic kidney disease pre-dialysis because, among other concerns, CMs also can increase phosphorus levels. Further, CMs cause hypocalcemia and are provided together with a vitamin D analog (AVD) to both prevent hypocalcemia and to help in suppression of serum PTH. (See Finch et al., Am J. Physiol Renal Physiol 298: F1315-F1322; De Schutter et al., Calcif Tissue Int (2012) 91:307-315; and Jung et al., J. Hypertension, Vol. 30, No. 11, November 2012, 2182-2191). Often CMs are employed when an AVD by itself is unable to suppress the PTH without also causing hypercalcemia. Thus, both a CM and an AVD may be administered to treat SHPT in some subjects.

Thus, therapies that can suppress PTH with minor effects on calcium and phosphate metabolism would be an ideal tool for the control and treatment of secondary hyperparathyroidism. Here, a combination therapy for treating SHPT using a highly potent active vitamin D analog (AVD), namely, 2-methylene-19-nor-(20S)-1α,25-dihydroxyvitamin $D_3$, referred to herein as "2MD" together with a calcimimetic is proposed to suppress serum PTH while maintaining serum calcium in the normal range. (See also U.S. Published Application No. 2014/0005152, the content of which is incorporated herein by reference in its entirety). As such, 2MD together with calcimimetics (CMs) may be useful for treating SHPT in subjects. Here, it is proposed that by administering a combination therapy of 2MD and a CM, a lower dose of 2MD and/or a lower dose of CM may be administered in order to treat SHPT, than the doses that are administered when 2MD and/or the CM are administered alone to treat SHPT. As such, synergy may be observed in the disclosed combination therapy for SHPT using 2MD and a CM. In addition, the disclosed combination therapy may be utilized to avoid the undesirable side effects associated with administering a higher dose of 2MD (e.g., hypercalcemia) and/or the undesirable side effects associated with administering a higher dose of a CM (e.g., hypocalcemia, overly low serum parathyroid hormone levels, nausea, and vomiting) than the lower doses administered in the disclosed combination therapy.

SUMMARY

Disclosed herein are pharmaceutical compositions comprising the vitamin D analog 2-methylene-19-nor-(20S)-1α, 25-dihydroxyvitamin $D_3$ (2MD) and a calcimimetic and methods for treating secondary hyperparathyroidism (SHPT) and/or the symptoms thereof using a combination therapy that includes administering low doses of the 2MD and a calcimimetic. The disclosed pharmaceutical compositions and combination therapy are suggested for treating secondary hyperparathyroidism as well as symptoms of secondary hyperparathyroidism when administered under well-controlled conditions to a subject in need thereof. Also disclosed herein are pharmaceutical compositions and combination therapy for preventing SHPT and/or the symptoms thereof which comprise and/or utilize the vitamin D analog 2MD and a calcimimetic. The disclosed combination therapy is suggested for preventing secondary hyperparathyroidism as well as symptoms of secondary hyperparathyroidism when administered under well-controlled conditions to a subject in need thereof. Preferably, in the disclosed methods using combination therapy, SHPT and/or the symptoms thereof are treated without inducing undesirable side effects in the subject. The potential undesirable side effects of 2MD may include hypercalcemia and oversuppression of serum PTH. The undesirable side effects of calcimimetics include hypocalcemia, overly low serum parathyroid hormone levels, nausea, and/or vomiting.

In the disclosed methods using a combination therapy, 2MD may be administered before, concurrently with, and/or after the calcimimetic. In particular, 2MD and/or the calcimimetic may be formulated together in an oral, topical, transdermal, parenteral, injectable or infusable form of a pharmaceutical composition comprising a suitable dose of 2MD and/or the calcimimetic.

DETAILED DESCRIPTION

Figure 1:
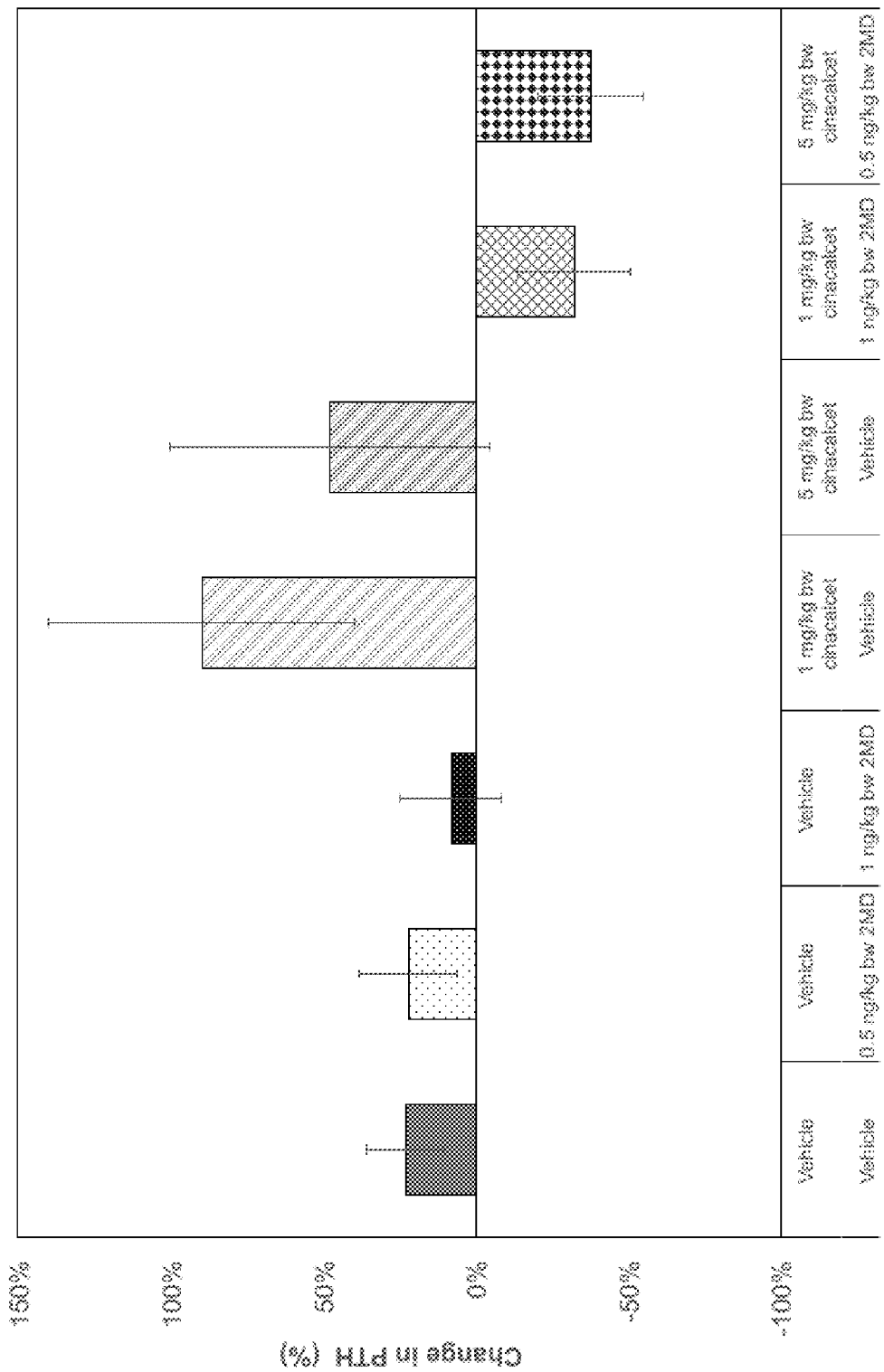
FIG. 1. Synergistic activity of oral formulation 2MD and cinacalcet administered daily in reducing serum PTH levels in vitamin D-deficient rats.
Figure 2:
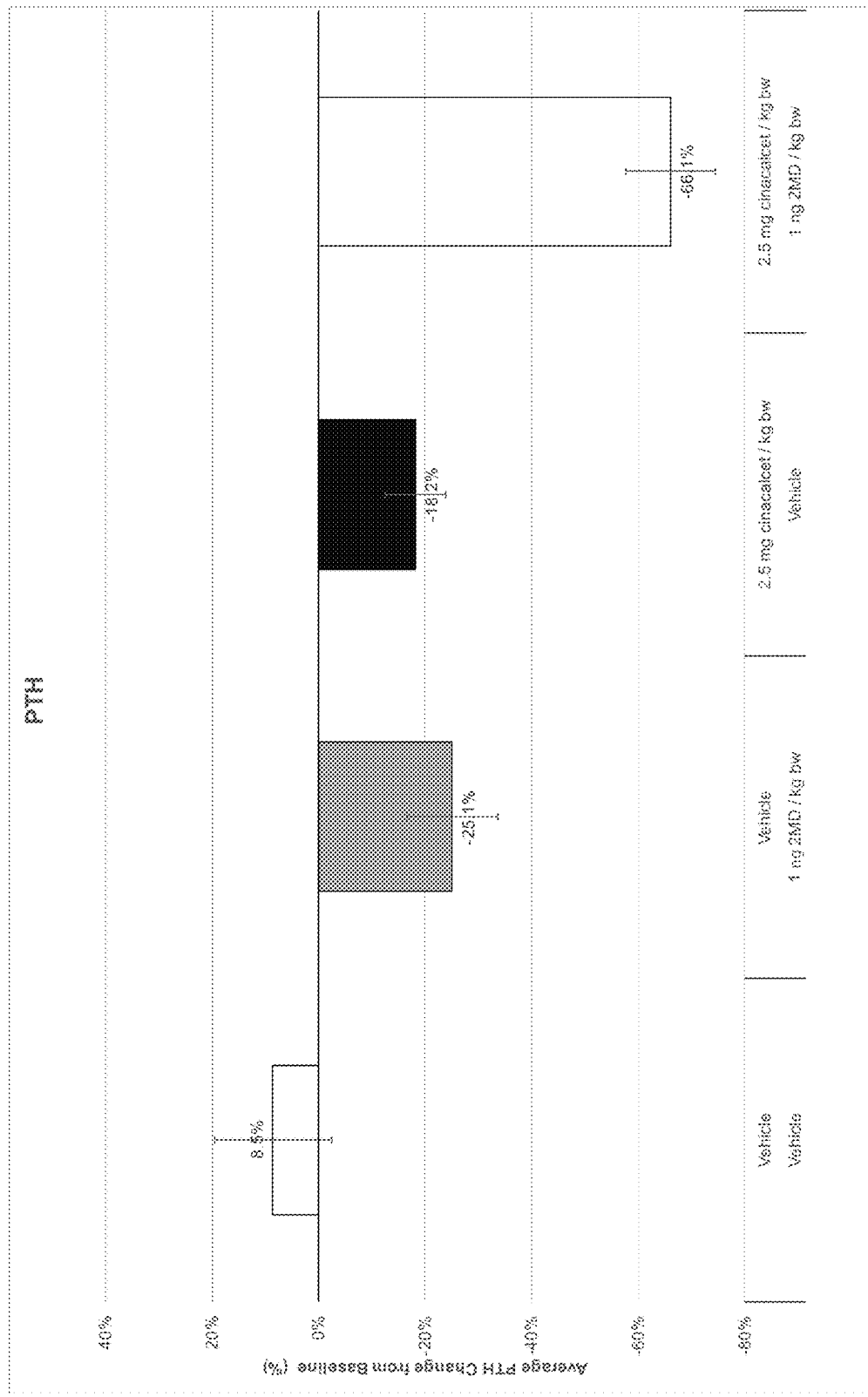
FIG. 2. Synergistic activity of oral formulation of 2MD and cinacalcet administered three times per week in reducing serum PTH levels in vitamin D-deficient rats.
Figure 3:
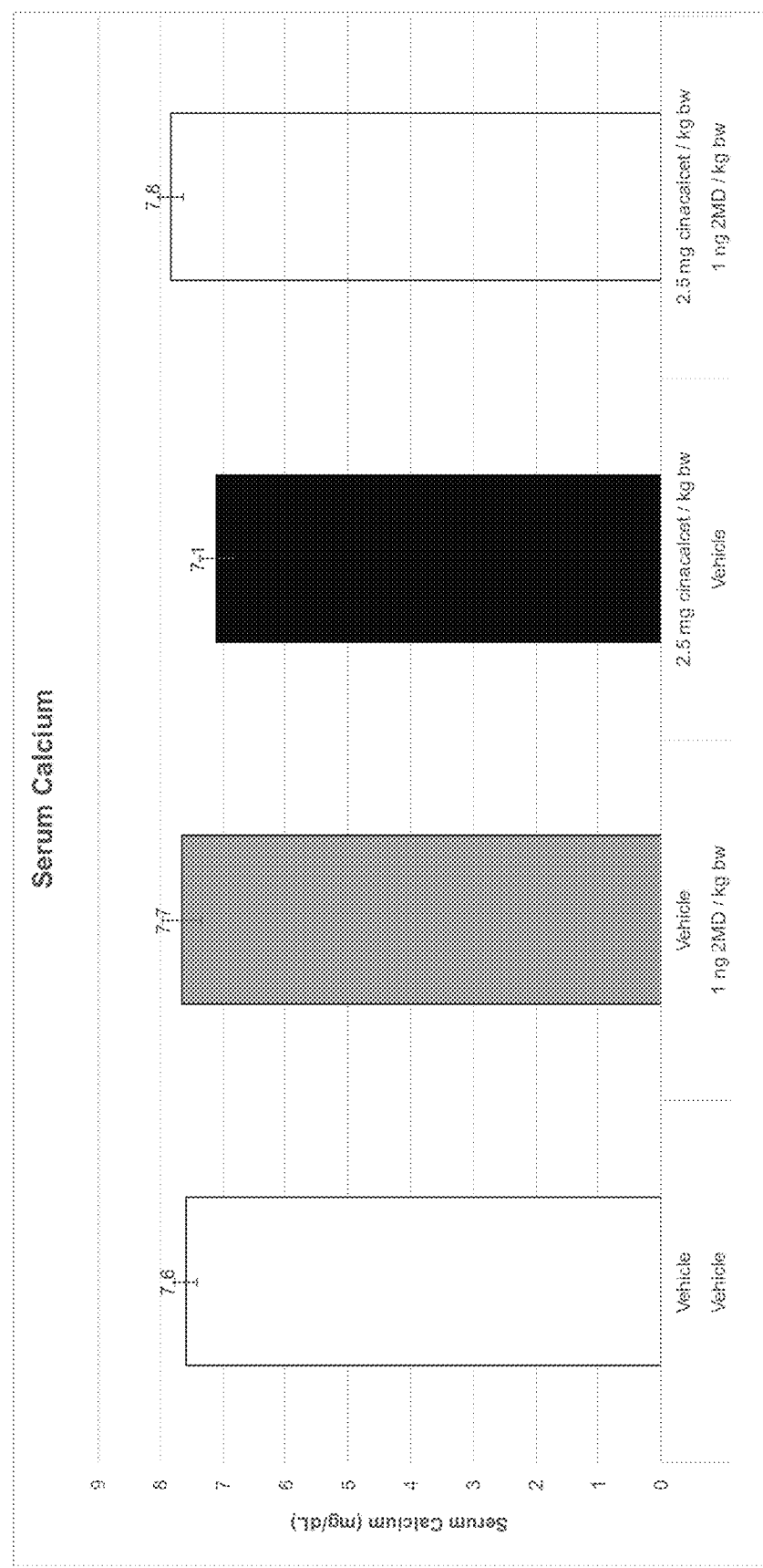
FIG. 3. Normal serum calcium levels in vitamin D-deficient rats treated as in FIG. 2.
Figure 4:
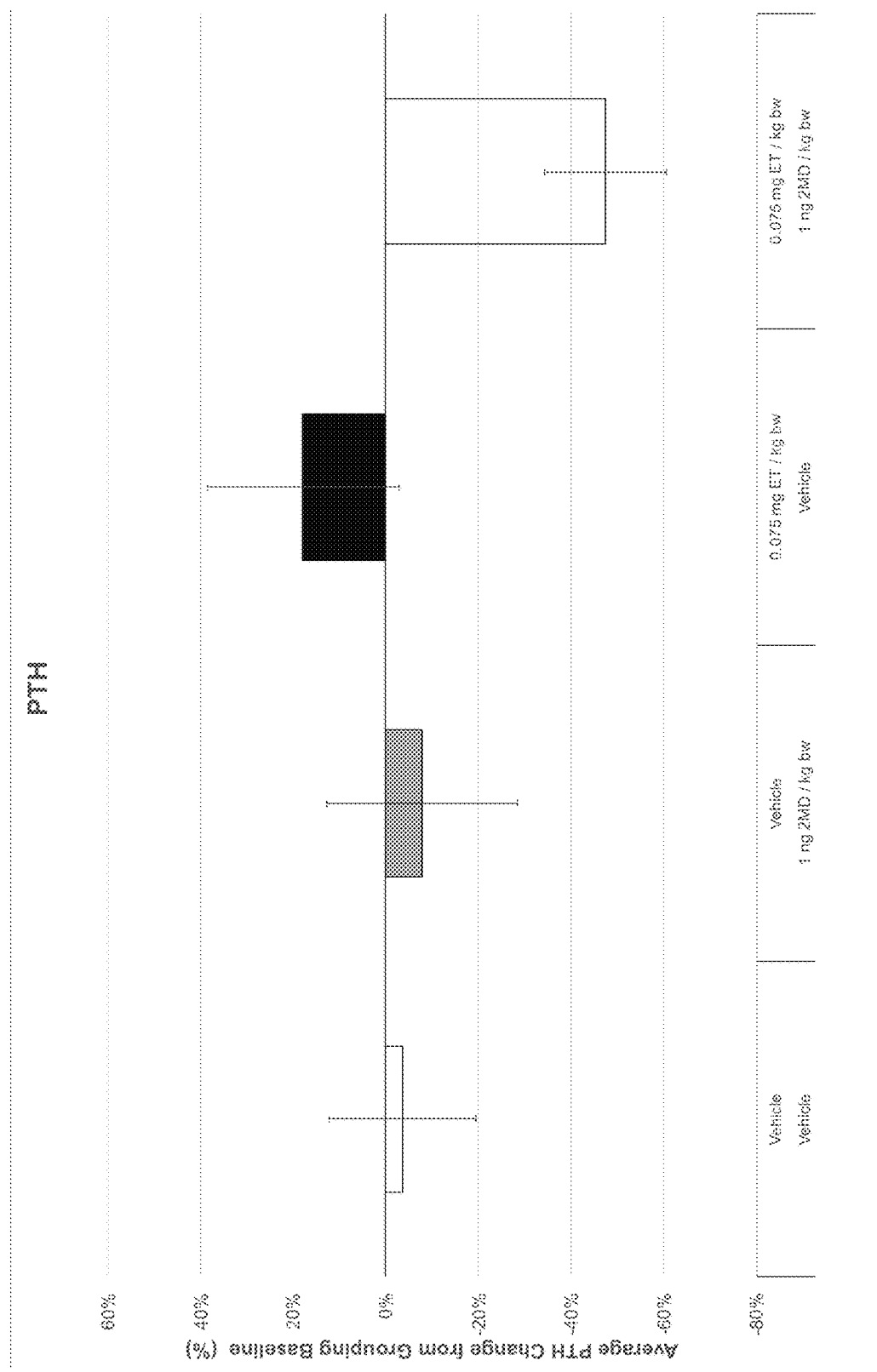
FIG. 4. Synergistic activity of intravenous formulation of 2MD and etecalcitide in reducing serum PTH levels in vitamin D-deficient rats.

Disclosed are methods of treating and/or preventing secondary hyperparathyroidism or the symptoms thereof, including treating and/or preventing secondary hyperparathyroidism and/or the symptoms thereof in a subject previously treated with a calcimimetic. The disclosed methods further may described as follows based on the following definitions.

As used in this specification and the claims, the singular forms "a," "an," and "the" include plural forms unless the content clearly dictates otherwise. For example, "an active vitamin D compound" or "AVD" (such as 2MD) should be interpreted to mean "one or more AVDs," and "a calcimimetic" or "CM" should be interpreted to mean "one or more CMs."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

As used herein, the term "subject," which may be used interchangeably with the terms "patient" or "individual," refers to one who receives medical care, attention or treatment and may encompass a human patient. The disclosed methods may be utilized to treat and/or prevent secondary hyperthyroidism of the symptoms thereof in a subject in need thereof. A subject in need thereof may include, but is not limited to, a subject having or at risk for developing secondary hyperthyroidism subsequent to a renal disease or disorder. A subject in need thereof may include a subject having a glomerular filtration rate (GFR) of less than about 30 or about 15 mL/min/1.73 m². A subject in need thereof may include, but is not limited to, a subject having or at risk for developing secondary hyperthyroidism subsequent to renal osteodystrophy, for example, due to renal failure. A subject in need thereof may include a subject undergoing renal dialysis. A subject in need thereof may include a subject undergoing peritoneal dialysis. A subject in need thereof may include, but is not limited to, a subject having or at risk for developing secondary hyperthyroidism as a result of a gastrointestinal malabsorption syndromes (e.g., chronic pancreatitis, small bowel disease, and malabsorption-dependent bariatric surgery in which the intestines do not absorb vitamins and minerals properly). A subject in need thereof may include, but is not limited to, a subject having or at risk for developing secondary hyperthyroidism as a result of a long-term lithium therapy, vitamin D deficiency, malnutrition, vitamin D-resistant rickets, or hypermagnesemia (i.e., abnormally high blood magnesium levels).

The disclosed methods may be utilized to treat and/or prevent the symptoms of secondary hyperthyroidism in a subject in need thereof. Symptoms of secondary hyperthyroidism treated and/or prevented by the disclosed methods may include, but are not limited to: increased levels of serum PTH, serum phosphorus, and serum creatinine. Other symptoms of secondary hyperthyroidism treated and/or prevented by the disclosed methods may include: weakening of the bones; calciphylaxis (when calcium forms clumps in the skin and lead to ulcers and potentially death of surrounding tissue); cardiovascular complications; abnormal fat and sugar metabolism; itching (pruritis); and low blood counts (anemia). Further symptoms of secondary hyperthyroidism treated and/or prevented by the disclosed methods may include: bone and joint pain, bone deformities, broken bones (fractures), swollen joints, kidney stones, increased urination, muscle weakness and pain, nausea, and loss of appetite. Even further symptoms of secondary hyperthyroidism treated and/or prevented by the disclosed methods may include: fatigue, upper abdominal pain, and depression.

Previously, it has been demonstrated that calcitriol administered through the diet can effectively prevent renal disease and renal failure by reducing the symptoms of renal disease. (See James Wonkee Kim. Effects of calcitriol on the MRL/MpJ-fas/lpr model of systemic lupus erythematosus (Ph.D. Thesis, University of Wisconsin-Madison (2009)). For instance, it has been previously shown that administering calcitriol completely prevents proteinuria in the MRL/MpJ-FAS$^{lpr}$ (MRL/lpr) mouse model of systemic lupus erythematosus (SLE). (See id.). However, severe hypercalcemia always accompanied this treatment. Hypercalcemia (i.e., increased levels of calcium in the blood) can result in serious physical problems, including death. Specifically, an increase in calcium of approximately 2 mg/100 ml is considered mild hypercalcemia and is not considered a problem. However, an increase in calcium levels of more than 2 mg/100 ml is considered severe hypercalcemia and can cause calcification of the kidney, heart, and aorta. Clearly, the use of this compound is not optimal to treat or prevent secondary hyperparathyroidism, or the symptoms thereof, because of the resultant hypercalcemia.

2-methylene-19-nor-(20S)-1α,25-dihydroxyvitamin $D_3$ (2MD) is an analog of $1,25(OH)_2D_3$ which has been shown to have increased in vivo potency toward bone but not on intestinal calcium absorption. The overall synthesis of 2MD is illustrated and described more completely in U.S. Pat. No. 5,843,928, issued Dec. 1, 1998, and entitled "2-Alkylidene-19-Nor-Vitamin D Compounds" the specification of which is specifically incorporated herein by reference. The biological activity of 2MD is also reported in U.S. Pat. No. 5,843,928 and in Shevde et al., "A Potent Analog of 1α,25-dihydroxyvitamin $D_3$ Selectively Induces Bone Formation" PNAS, Vol. 99, No. 21 pp 13487-13491 (2002), both of which are specifically incorporated herein by reference.

Surprisingly, in the methods disclosed herein, 2MD can be administered and a calcimimetic can be administered to a subject to treat and/or prevent secondary hyperparathyroidism and/or its accompanying symptoms preferably without causing undesirable side effects in the subject, which undesirable side effects for 2MD may include hypercalcemia and which undesirable side effects for a calcimimetic may include hypocalcemia.

As used herein, "hypercalcemia" means elevated calcium levels in the blood. In a normal subject, calcium levels are approximately 8.5-10.5 mg/dL or 2.2-2.6 mmol/L. As such, calcium levels greater than about 10.5 mg/dL or 2.6 mmol/L may be indicative of hypercalcemia. In cases of severe hypercalcemia (i.e., calcium levels above 15-16 mg/dL or 3.75-4 mmol/L) coma and cardiac arrest can develop. In the methods disclosed herein, 2MD can be administered to treat and/or prevent secondary hyperparathyroidism and/or its accompanying symptoms including elevated PTH levels, elevated phosphorus levels, and elevated creatinine levels. As used herein, "hypocalcemia" means decreased calcium levels in the blood. Calcium levels less than about 9 mg/dL or 2.2 mmol/L may be indicative of hypocalcemia. Hypocalcemia is a contraindication of calcimimetics and calcimimetics should not be administered to subjects having a calcium level of 8 mg/dL or less.

Undesirable side effects of calcimimetics may also include overly low serum parathyroid hormone levels. For example, an undesirable side effect of calcimimetics may include a reduction of serum parathyroid hormone levels to less than about 100 pg/mL, which may lead to adynamic bone disease. Undesirable side effects of calcimimetics may also include nausea and vomiting.

Also in the methods disclosed herein, 2MD and a calcimimetic can be administered to reduce the severity of secondary hyperparathyroidism of renal disease and its accompanying symptoms in a subject in need thereof without causing severe hypercalcemia or oversuppression of PTH, by reducing PTH phosphorus, and creatinine levels in blood to normal levels.

The present invention therefore provides novel methods of treating and/or preventing secondary hyperparathyroidism and/or its accompanying symptoms in a subject at risk of developing secondary hyperparathyroidism, and of treating and/or preventing secondary hyperparathyroidism and/or its accompanying symptoms in a subject exhibiting symptoms of secondary hyperparathyroidism, by administering to the subject a therapeutically effective amount of 2-methylene-19-nor-(20S)-1α,25-dihydroxyvitamin $D_3$ (2MD) or pharmaceutically acceptable salts thereof preferably without inducing an undesirable side effect in the subject, where 2MD has the structure (I):

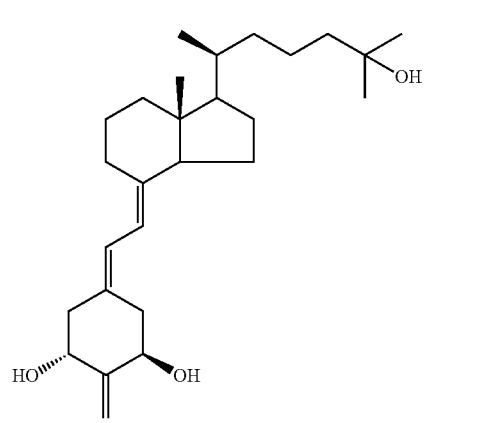

In the disclosed methods, the subject is administered 2MD and a calcimimetic (e.g., in order to treat and/or prevent secondary hyperparathyroidism and/or the symptoms thereof). For example, 2MD may be administered to the subject before, concurrently, or after the calcimimetic is administered to the subject.

As utilized herein, a calcimimetic is an agent that mimics the effect of calcium on the parathyroid gland. As such, calcimimetics increase the sensitivity of the calcium-sensing receptor (CaR) to circulating serum calcium, reducing the secretion of PTH and the serum calcium concentration.

Calcimimetics administered in the disclosed methods may include, but are not limited to, the compound named (R)—N-[1-(1-naphthyl)ethyl]-3-[3-(trifluoromethyl)phenyl] propan-1-amine otherwise referred to as "cinacalcet," trade name "Sensipar®" and having the structure:

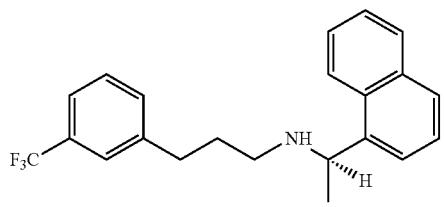 [SMILES: C[C@@H](NCCCc1cccc(C(F)(F)F)c1)c1cccc2ccccc12]

or pharmaceutical salts thereof.

Calcimimetics administered in the disclosed methods also may include, but are not limited to, the compound referred to as "etelcalcetide," "AMG 416," "velcalcetide," and "KAI-4169" and having the structure:

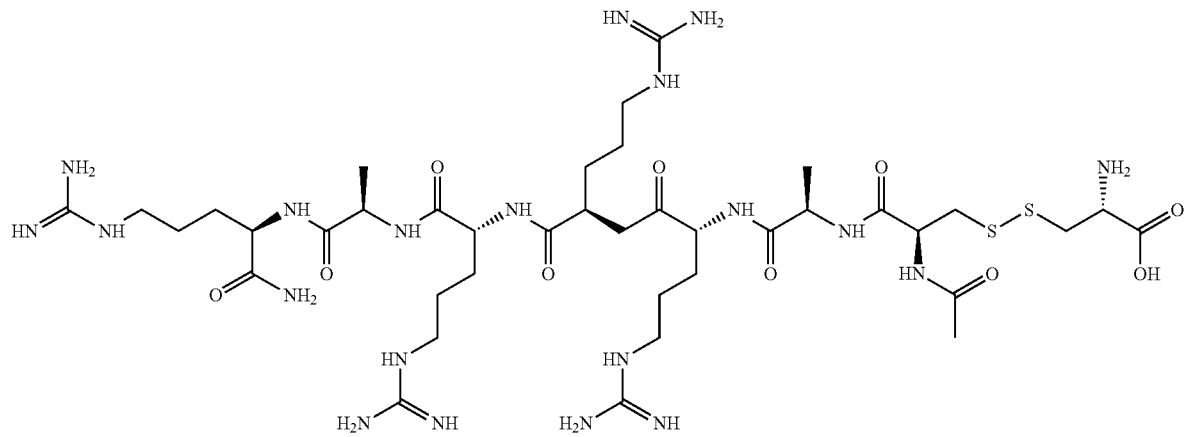 [SMILES: CC(=O)N[C@H](CSSC[C@H](N)C(=O)O)C(=O)N[C@H](C)C(=O)N[C@H](CCCNC(=N)N)C(=O)C[C@H](CCCNC(=N)N)C(=O)N[C@H](CCCNC(=N)N)C(=O)N[C@H](C)C(=O)N[C@H](CCCNC(=N)N)C(N)=O]

or pharmaceutical salts thereof.

As used herein, "treat," "treating" or "treatment" means amelioration, alleviation or ablation of a clinical symptom indicative of secondary hyperparathyroidism. Amelioration, alleviation or ablation of a clinical symptom includes, for example, arresting, reducing the severity of or slowing the progression of or causing the regression of a symptom of secondary hyperparathyroidism. For instance, lowering the amount of serum PTH, serum phosphorus or serum creatinine levels in response to treatment with 2MD and a calcimimetic. Specifically, treating may include reducing the amount of serum PTH (e.g., below 300 pg/ml), serum phosphorus or serum creatinine pre-treatment versus post-treatment by at least about 20%, 30%, 40%, 50%, 60%, 70%, 80%, 90% or more relative to the level of serum PTH, serum phosphorus, or serum creatine prior to treatment or relative to a control. Other pathological conditions, chronic complications or phenotypic manifestations of secondary hyperparathyroidism are known to those skilled in the art and can similarly be used as a measure of treating secondary hyperparathyroidism so long as there is a reduction in the severity of the condition, complication or manifestation associated with the disease.

As used herein, "preventing" means forestalling of a clinical symptom indicative of secondary hyperparathyroidism. Such forestalling includes, for example, the maintenance of normal kidney functions in a subject at risk of developing secondary hyperparathyroidism prior to the development of overt symptoms of secondary hyperparathyroidism including, but not limited to, increased levels of serum PTH (e.g., preventing a rise of serum PTH above about 300 pg/ml), phosphorus and creatinine. Therefore, the term "preventing" includes the prophylactic treatment of subjects to guard them from the occurrence of secondary hyperparathyroidism. Preventing secondary hyperparathyroidism in a subject is also intended to include inhibiting or arresting the development of secondary hyperparathyroidism. Inhibiting or arresting the development of secondary hyperparathyroidism includes, for example, inhibiting or arresting the occurrence of increased levels of serum PTH, phosphorus and creatinine.

As used herein, a "renal disease" or a "renal disorder" means a condition exhibiting impaired kidney function in a subject who is not on dialysis or a subject with chronic kidney disease (CKD) at stages 2 or 3, such as, for instance, acute kidney failure, acute nephritic syndrome, analgesic nephropathy, atheroembloic renal disease, chronic kidney failure, chronic nephritis, congenital nephrotic syndrome, goodpasture syndrome, interstitial nephritis, kidney cancer, kidney damage, kidney infection, kidney injury, kidney stones, membranoproliferative GNI, membranoproliferative GNII, membranous nephropathy, minimal change disease, necrotizing glomerulonephritis, nephroblastoma, nephrocalcinosis, nephrogenic diabetes insipidus, nephropathy-IgA, nephrosis nephrotic syndrome, polycystic kidney disease, post-strepococcal GN, reflux nephropathy, renal artery embolism, renal artery stenosis, renal disorders, renal papillary necrosis, renal tubular acidosis type I, renal tubular acidosis type II, renal underperfusion, renal vein thrombosis.

"Renal disease" is meant to include subjects with established kidney failure (e.g., a glomerular filtration rate (GFR) of less than about 30 or about 15 mL/min/1.73 m$^2$ or permanent renal replacement therapy (RRT)). A subject having "renal disease" is meant to include a subject who has had kidney damage for more than 3 months, as defined by structural or functional abnormalities of the kidney, with or without decreased GFR, manifested by either pathological abnormalities or markers of kidney damage, including abnormalities in the composition of the blood or urine, or abnormalities in imaging tests. Markers of kidney damage include proteinuria of greater than 300 μg/day as measured by 24-HR excretion method. (See Table 15, Am. J. of Kidney Diseases, v. 39, no. 2, Suppl. 1 (February 2002), pp. 546-575, incorporated herein by reference). This definition may include subjects on dialysis, such as renal dialysis and/or peritoneal dialysis.

As used herein, a subject having "stage 2 chronic kidney disease (CKD)" means a subject exhibiting a mild reduction in GFR (60-89 mL/min/1.73 m$^2$). Kidney damage is defined as pathologic abnormalities or markers of damage, including abnormalities in blood or urine test or imaging studies. A subject having "stage 3 chronic kidney disease (CKD)" means a subject exhibiting a moderate reduction in GFR (30-59 mL/min/1.73 m$^2$). Guidelines for characterizing kidney disease may distinguish between stage 3A (GFR 45-59) and stage 3B (GFR 30-44) for purposes of screening and referral. For more information about stages of kidney disease, see Am. J. of Kidney Disease, V. 39, No. 2, Suppl. 1, Feb. 2002, incorporated herein by reference. "Renal failure" is evidenced by a decreased glomeruli filtration rate (GFR) from a high value of 110 ml/minute/1.73 m$^2$ to 30 ml/minute/1.73 m$^2$ where dialysis is often initiated, and may be referred to as Stage 5, Chronic Kidney Disease (CKD).

As used herein, "administering" mean introducing a compound into the body, preferably into the systemic circulation, as described in more detail below. Examples include but are not limited to oral, topical, buccal, sublingual, pulmonary, transdermal, transmucosal, as well as subcutaneous, intraperitoneal, intravenous, and intramuscular injection or in the form of liquid or solid doses via the alimentary canal.

As used herein, "therapeutically effective" means an amount of a compound that, when administered to a subject for treating or preventing a disease, is sufficient to effect such treatment of prevention of the disease. A "therapeutically effective amount" will vary depending on the compound, the disease state being treated, the severity or the disease treated, the age and relative health of the subject, the route and form of administration, the judgment of the attending medical or veterinary practitioner, and other factors.

In the disclosed treatment and prevention methods, a subject in need thereof may be administered an effective dose level of 2MD. An effective dose level of 2MD for use in accordance with the disclosed methods is high enough for achieving a desired therapeutic effect (e.g., reduction in serum PTH, serum phosphorus, and/or serum creatine) and low enough so as not as to cause an undesired side effect (e.g., hypercalcemia).

In some embodiments, the subject may be administered a dose of 2MD as low as 10 ng, 27.5 ng, 55 ng, 110 ng, 220 ng, 330 ng, 440 ng, 550 ng, or 660 ng, daily or no more than 3 times per week in order to treat and/or prevent secondary hyperparathyroidism and/or to treat or prevent the symptoms thereof in a subject. In some embodiments, the subject may be administered a dose of 2MD as high as 27.5 ng, 55 ng, 110 ng, 220 ng, 330 ng, 440 ng, 550 ng, 660 ng, or 770 ng, daily or no more than 3 times per week in order to treat and/or prevent secondary hyperparathyroidism and/or to treat or prevent the symptoms thereof in a subject. Minimal and/or maximal doses of 2MD may include doses falling within dose ranges having as end-points any of these disclosed doses (e.g., 55 ng-110 ng). In the disclosed methods of combination therapy with a calcimimetic, 2MD may be administered in lower doses (e.g., ngs) than the doses in which 2MD is administered without a calcimimetic.

In some embodiments, a minimal dose level of 2MD for achieving therapy may be at least about 0.05, 0.1, 0.25, 0.5, 1.0, 2.0, 2.5, 3.0, 4.0, 5.0, 10.0, 12.5, 15.0, or 20.0 ng/kg body weight of the subject. In some embodiments, a maximal dose level of 2MD for achieving therapy may not exceed about 20.0, 15.0, 12.5, 10.0, 5.0, 4.0, 3.0, 2.5, 2.0 1.0, 0.5, 0.25, 0.1, 0.05 ng/kg body weight of the subject. Minimal and/or maximal dose levels of 2MD for achieving therapy may include dose levels falling within ranges having as end-points any of these disclosed dose levels (e.g., 0.25-1.0 ng/kg body weight of the subject). In the disclosed methods of combination therapy with a calcimimetic, 2MD may be administered at lower dose levels (e.g., ng/kg) than the dose levels in which 2MD is administered without a calcimimetic.

In the disclosed treatment and prevention methods, a subject in need thereof may be administered an effective dose level of a calcimimetic. An effective dose level of a calcimimetic for use in accordance with the disclosed methods is high enough for achieving a desired therapeutic effect and low enough so as not as to cause an undesired side effect (e.g., hypocalcemia, overly low levels of serum parathyroid hormone, nausea, and/or vomiting).

In some embodiments, the subject may be administered a dose of a calcimimetic as low as 0.5625 mg, 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week (or no more than three times per week) in order to treat secondary hyperparathyroidism and/or to treat or prevent the symptoms thereof in a subject. In some embodiments, the subject may be administered a dose of a calcimimetic as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week (or no more than three times per week) in order to treat secondary hyperparathyroidism and/or to treat or prevent the symptoms thereof in a subject. Minimal and/or maximal doses of the calcimimetic may include doses falling within dose ranges having as end-points any of these disclosed doses (e.g., 2.5 mg-200 mg). In the disclosed methods of combination therapy with 2MD, the calcimimetic may be administered in lower doses (e.g., mgs) than the doses in which the calcimimetic is administered without 2MD.

In some embodiments, a minimal dose level of a calcimimetic for achieving therapy may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a calcimimetic for achieving therapy may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the calcimimetic for achieving therapy may include dose levels falling within ranges having as end-points any of these disclosed dose levels (e.g., 500-2000 ng/kg body weight of the subject). In the disclosed methods of combination therapy with 2MD, the calcimimetic may be administered at lower dose levels (e.g., ng/kg or mg/kg) than the dose levels in which the calcimimetic is administered without 2MD.

In some embodiments, the calcimimetic administered in the disclosed methods is cinacalcet. Cinacalcet comes in tablet form in three strengths: 30 mg, 60 mg, and 90 mg. The tablets may be split to provide half-strengths. Cinacalcet typically is prescribed in doses from about 15 mg (i.e., a half of the 30 mg tablet) to about 90 mg, once, twice, three times or four times daily. In the disclosed methods of combination therapy with 2MD, cinacalcet may be administered in lower doses (e.g., mgs) than the doses in which cinacalcet is administered without 2MD. In the disclosed methods of combination therapy with 2MD, cinacalcet may be administered at lower dose levels (e.g. ng/kg) than the doses in which cinacalcet is administered without 2MD. In addition, when cinacalcet is administered together with 2MD, the cinacalcet may be administered three times per week instead of daily or several time daily.

In some embodiments, the calcimimetic administered in the disclosed methods is etelcalcetide. Etelcalcetide is administered intravenously typically in doses ranging from 2.5 mg to 15 mg, three times per week. In the disclosed methods of combination therapy with 2MD, etelcalcetide may be administered in lower doses (e.g., mgs) than the doses in which etelcalcetide is administered without 2MD. In the disclosed methods of combination therapy with 2MD, etelcalcetide may be administered at lower dose levels (e.g., ng/kg) than the doses in which etelcalcetide is administered without 2MD. In the disclosed methods of combination therapy with 2MD, etelcalcetide may be administered at lower frequency (e.g., <3 times week), than when etelcalcetide is administered alone.

2MD and/or a calcimimetic may be the active pharmaceutical ingredient (API) administered in the disclosed methods. The API may be administered orally, topically, parenterally or transdermally or by inhalation. The compound may be administered by injection or intravenous infusion using suitable sterile solutions. Topical dosage forms may be creams, ointments, patches, or similar vehicles suitable for transdermal and topical dosage forms. Preferably for the treatment of secondary hyperparathyroidism, or for the treatment or prevention of the symptoms of secondary hyperparathyroidism, 2MD and/or the calcimimetic is administered either orally or parenterally (i.v.). The dose may be properly selected in accordance with the specific route of administration.

As used herein, "oral dosage" forms may include capsules (i.e., a solid oral dosage form consisting of a shell and a filling), whereby the shell is composed of a single sealed enclosure, or two halves that fit together and which are sometimes sealed with a band, and whereby capsule shells may be made from gelatin, starch, or cellulose, or other suitable materials, may be soft or hard, and are filled with a solid or liquid ingredients that can be poured or squeezed. The oral dosage form may also be a capsule or coated pellets, in which the drug is enclosed within either a hard or soft soluble container or "shell" made from a suitable form of gelatin. The drug itself may be in the form of granules to which varying amount of coating have been applied or in a capsule coated extended release, in which the drug is enclosed within either a hard or soft soluble container or "shell" made from a suitable form of gelatin. Additionally, the capsule may be covered in a designated coating which releases a drug or drugs in such a manner to allow at least a reduction in dosing frequency as compared to that drug or drugs presented as a conventional dosage form.

The oral dosage form may further be a capsule delayed release, in which the drug is enclosed within either a hard or soft soluble container made from a suitable form of gelatin, and which releases a drug (or drugs) at a time other than promptly after administration, whereby enteric-coated articles are delayed release dosage forms. Capsule delayed release pellets, in which the drug is enclosed within either a hard or soft container or "shell" are also useful. In these cases, the drug itself is in the form of granules to which enteric coating has been applied, thus delaying release of the drug until its passing into the intestine. Capsule extended release and capsule film-coated extended release are also useful.

Additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule).

Typically, the active ingredients may be dissolved or suspended in a liquid vehicle, a granule (a small particle or grain), a pellet (a small sterile solid mass consisting of a highly purified drug, with or without excipients, made by the formation of granules, or by compression and molding), or a pellet coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form).

Other forms include pills (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), syrup (an oral solution containing high concentrations of sucrose or other sugars; the term has also been used to include any other liquid dosage form prepared in a sweet and viscid vehicle, including oral suspensions), tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant aftertaste), tablet coated or tablet delayed release, tablet dispersible, tablet effervescent, tablet extended release, tablet film coated, or tablet film coated extended release where the tablet is formulated in such manner as to make the contained medicament available over an extended period of time following ingestion.

In other forms, a tablet for solution, tablet for suspension, tablet multilayer, tablet multilayer extended release may be provided, where the tablet is formulated in such manner as to allow at least a reduction in dosing frequency as compared to that drug presented as a conventional dosage form. A tablet orally disintegrating, tablet orally disintegrating delayed release, tablet soluble, tablet sugar coated, osmotic, and the like are also suitable.

The oral dosage form composition may contain an active pharmaceutical ingredient and one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (e.g., anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)

(7). Alcohol is a good example of an ingredient that may be considered either active or inactive depending on the product formulation.

The disclosed oral formulations may include single formulations comprising a combination of a low dose of 2MD and a low dose of a calcimimetic. For example, the disclosed oral formulation may include a single formulation comprising a combination of a low dose of 2MD (e.g., 10 ng, 27.5 ng, 55 ng, 110 ng, 220 ng or ranges bounded by endpoints of any of these values) and a low dose of cinacalcet (e.g., 0.5625 mg, 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, or 90 mg or ranges bounded by endpoints of any of these values).

As used herein, the injectable and infusion dosage forms include, but are not limited to, a liposomal injectable, which either consists of or forms liposomes (a lipid bilayer vesicle usually composed of phospholipids which is used to encapsulate an active drug substance). An injection, which includes a sterile preparation intended for parenteral use; five distinct classes of injections exist as defined by the USP, is also suitable. An emulsion injection, which includes an emulsion consisting of a sterile, pyrogen-free preparation intended to be administered parenterally or a lipid complex injection are also suitable.

Other forms include a powder for solution injection, which is a sterile preparation intended for reconstitution to form a solution for parenteral use; a powder for suspension injection that is a sterile preparation intended for reconstitution to form a suspension for parenteral use; a powder lyophilized for liposomal suspension injection, which is a sterile freeze dried preparation intended for reconstitution for parenteral use which has been formulated in a manner that would allow liposomes (a lipid bilayer vesicle usually composed of phospholipids which is used to encapsulate an active drug substance, either within a lipid bilayer or in an aqueous space) to be formed upon reconstitution; a powder lyophilized for solution injection, which is a dosage form intended for the solution prepared by lyophilization ("freeze drying"), a process which involves the removal of water from products in the frozen state at extremely low pressures. This is intended for subsequent addition of liquid to create a solution that conforms in all respects to the requirements for injections; a powder lyophilized for suspension injection being a liquid preparation, intended for parenteral use that contains solids suspended in a suitable fluid medium and conforms in all respects to the requirements for Sterile Suspensions; the medicinal agents intended for the suspension are prepared by lyophilization ("freeze drying"), a process which involves the removal of water from products in the frozen state at extremely low pressures; a solution injection being a liquid preparation containing one or more drug substances dissolved in a suitable solvent or mixture of mutually miscible solvents that is suitable for injection; a solution concentrate injection being a sterile preparation for parenteral use which, upon the addition of suitable solvents, yields a solution conforming in all respects to the requirements for injections.

A suspension injection comprises a liquid preparation, suitable for injection, which consists of solid particles dispersed throughout a liquid phase in which the particles are not soluble that can also consist of an oil phase dispersed throughout an aqueous phase, or vice-versa. A suspension liposomal injection comprises a liquid preparation, suitable for injection, which consists of an oil phase dispersed throughout an aqueous phase in such a manner that liposomes (a lipid bilayer vesicle usually composed of phospholipids which is used to encapsulate an active drug substance, either within a lipid bilayer or in an aqueous space) are formed. A suspension sonicated injection comprises a liquid preparation, suitable for injection, which consists of solid particles dispersed throughout a liquid phase in which the particles are not soluble. In addition, the product is sonicated while a gas is bubbled through the suspension, and this results in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives. Formulations suitable for parenteral administration conveniently comprise a sterile oily or aqueous preparation of the active ingredient which is preferably isotonic with the blood of the recipient.

The disclosed injectable formulation may include intravenous (IV) formulations. The IV formulation may include single formulations comprising a combination of a low dose of 2MD and a low dose of a calcimimetic. For example, the disclosed oral formulation may include a single formulation comprising a combination of a low dose of 2MD (e.g., 10 ng, 27.5 ng, 55 ng, 110 ng, 220 ng or ranges bounded by endpoints of any of these values) and a low dose of etecalcitide (e.g., 0.5625 mg, 1.25 mg, 2.5 mg, 5 mg, 7.5 mg, or 10 mg or ranges bounded by endpoints of any of these values).

EXAMPLE

The following Example is illustrative and should not be interpreted to limit the scope of the claimed subject matter.

Example 1—Synergistic Activity of 2MD and Cinacalcet

Male rats were made vitamin D-deficient. Subsequently, the vitamin D-deficient rats were administered orally 1× daily 2MD and/or cinacalcet for 10 days. Blood was collected prior to the first dose and 24 hours after the $10^{th}$ dose was administered. Intact PTH was measured in serum samples and a percent change in PTH from pre-dose levels was determined. Results are illustrated in FIG. 1.

Furthermore, we now have results from experiments in which 2MD and/or an exemplary calcimimetic, "cinacalcet," were administered at various dose levels in an experimental rat model for secondary hyperparathyroidism. Our results demonstrate that 2MD and cinacalcet when concurrently administered exhibit synergy in reducing serum parathyroid hormone (PTH) levels. In an experimental rat model, male rats first were made vitamin D-deficient. Subsequently, the vitamin D-deficient male rats were administered orally 1× daily 2MD and/or cinacalcet for 10 days at various dose levels as indicated in FIG. 1. Blood was collected prior to the first dose and 24 hours after the $10^{th}$ dose was administered. Intact parathyroid hormone (PTH) was measured in serum samples and a percent change in PTH from pre-dose levels was determined. The results in FIG. 1 indicate that dose levels of 2MD as low as 1.0 ng/kg body weight or even as low as 0.5 ng/kg body weight could be administered to effect a decrease in serum PTH when cinacalcet at dose levels as low as 5 mg/kg body weight or 1 mg/kg body weight was administered concurrently with the 2MD.

This observation is surprising in view prior results which suggest that a dose level of 2MD greater than 1.0 ng/kg body weight is required in order to obtain a maximal reduction in serum PTH levels. (See, e.g., U.S. Pat. No. 9,034,853). Furthermore, our observation that a low dose of 2MD and a calcimimetic can be concurrently administered to treat secondary hyperparathyroidism has important implications for treating secondary hyperparathyroidism. Because 2MD may exhibit negative side-effects at high dosages which include hypercalcemia, our observation indicates that a relatively low dose of 2MD may be administered with a calcimimetic in order to reduce serum PTH levels without inducing hypercalcemia. In addition, because calcimimetics such as cinacalcet may exhibit negative side-effects at high dosages, our observation suggests that a relatively low dose of a calcimimetic may be administered with 2MD in order to reduce serum PTH levels without inducing negative side-effects.

Example 2—Combination Therapy of Low Dose Calcimimetic and Low Dose Vitamin D Analog in a Single Formulation for Oral or Intravenous Administration Thrice Weekly to Elicit Synergistic Activities Dose Preparation Oral Formulations.

Cinacalcet was weighed and mixed with ethanol (at least 21 mcL ethanol/mg cinacalcet) for approximately 10 minutes. After a clear solution was produced, the clear solution was mixed with an ethanolic solution of 2MD or vitamin D analog as a control. The two ethanolic solutions were mixed (approx. 15 min.) with Neobee oil so that there was no more than 14.1% of ethanol in the final dosing solution. Doses were delivered in a 0.75 mL/kg dose volume.

Intravenous Formulations.

Etelcalcitide was weighed and mixed with propylene glycol (up to 5 mg etelcalcitide/ml propylene glycol) for approximately 1 minute. After a clear solution was produced (~60 min), the clear solution was mixed with an ethanolic solution of 2MD or vitamin D analog as a control (no more than ~0.6% ethanol in the final solution) for approximately 1 min. Doses were delivered in a 1 mL/kg dose volume.

Synergistic Activity of Low Dose Calcimimetic and 2MD

Sprague-Dawley rats were made vitamin D-deficient and then placed on a high containing lactose (10%) and elevated levels of calcium (2%) and phosphorus (1.25%). After hyperparathyroidism was established in the rats, animals were administered cinacalcet or etelcalcitide, 2MD or the combination of the two thrice weekly for nearly four weeks. Blood was collected 48-72 hours after the last dose was given and PTH (Immutopics Intact PTH kit) and serum calcium (Perkin Elmer) measured. Suppression of PTH more than doubled when both agents were administered together in one formulation when compared to each compound given alone. Serum calcium was unaffected by administration of 1 ng 2MD/kg bw but decreased by 0.5 mg % when cinacalcet alone was given to the rats. The combination formulation resulted in calcium levels equivalent to the control animals. These results are important and indicate that a single oral formulation of a low dose of 2MD and a low dose of cinacalcet, or a single intravenous solution of a low dose of 2MD and a low dose of etecalcitide, could be administered to reduce serum PTH without deleteriously affect serum calcium levels.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue or prior invention.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method of treating secondary hyperparathyroidism or the symptoms thereof in a subject having secondary hyperparathyroidism or at risk for developing secondary hyperparathyroidism, the method comprising administering a single oral pharmaceutical composition to the subject that delivers to the subject a combination of (i) 2-methylene-19-nor-(20S)-1α,25-dihydroxyvitamin $D_3$ (2MD) or a pharmaceutically acceptable salt thereof and (ii) cinacalcet, wherein the dose level of 2MD delivered to the subject is no more than 1 ng/kg body weight and the dose level of the cinacalcet delivered to the subject is no more than 2.5 mg/kg body weight, and wherein secondary hyperparathyroidism or the symptoms thereof are treated without inducing hypercalcemia or hypocalcemia in the subject.

2. The method of claim 1, wherein the dose level of 2MD delivered to the subject is no more than 0.5 ng/kg body weight and the dose level of the cinacalcet delivered to the subject is no more than 1 mg/kg body weight.

3. The method of claim 1, wherein the dose level of 2MD delivered to the subject is no more than 0.25 ng/kg body weight and the dose level of the cinacalcet delivered to the subject is no more than 0.5 mg/kg body weight.

4. The method of claim 1, wherein the pharmaceutical composition is administered no more than three times per week.

5. The method of claim 1, wherein the subject has chronic kidney disease stage 5 (CKD-5D).

6. The method of claim 1, wherein the subject has kidney disease characterized by a glomeruli filtration rate (GFR) of less than about 30 ml/minute/1.73 m².

7. The method of claim 1, wherein the subject is receiving hemodialysis treatment.

8. The method of claim 1, wherein the subject is receiving peritoneal dialysis.

9. The method of claim 1, wherein the treated symptom of secondary hyperparathyroidism is elevated serum PTH and the elevated serum PTH is reduced to a serum level lower than about 300 pg/ml.

10. The method of claim 1, wherein the treated symptom of secondary hyperparathyroidism is elevated serum phosphorus.

11. The method of claim 1, wherein the treated symptom of secondary hyperparathyroidism is elevated serum creatinine.

12. The method of claim 1, wherein after treatment the subject has a serum calcium level of between 8.5-10.5 mg/dl.

13. A method of treating secondary hyperparathyroidism or the symptoms thereof in a subject having secondary hyperparathyroidism or at risk for developing secondary hyperparathyroidism, the method comprising administering a single intravenous pharmaceutical composition to the subject that delivers to the subject a combination of (i) 2-methylene-19-nor-(20S)-1α,25-dihydroxyvitamin $D_3$ (2MD) or a pharmaceutically acceptable salt thereof and (ii) etecalcitide, wherein the dose level of 2MD delivered to the subject is no more than 1 ng/kg body weight and the dose level of the etecalcitide delivered to the subject is no more than 0.075 mg/kg body weight, and wherein secondary hyperparathyroidism or the symptoms thereof are treated without inducing hypercalcemia or hypocalcemia in the subject.

14. The method of claim 13, wherein the dose level of 2MD delivered to the subject is no more than 0.5 ng/kg body weight and the dose level of the etecalcitide delivered to the subject is no more than 0.05 mg/kg body weight.

15. The method of claim 13, wherein the dose level of 2MD delivered to the subject is no more than 0.25 ng/kg body weight and the dose level of the etecalcitide delivered to the subject is no more than 0.025 mg/kg body weight.

16. The method of claim 13, wherein the pharmaceutical composition is administered no more than three times per week.

17. The method of claim 13, wherein the subject has chronic kidney disease—stage 5 (CKD-5D).

18. The method of claim 13, wherein the subject has kidney disease characterized by a glomeruli filtration rate (GFR) of less than about 30 ml/minute/1.73 m².

19. The method of claim 13, wherein the subject is receiving hemodialysis treatment.

20. The method of claim 13, wherein the subject is receiving peritoneal dialysis.

21. The method of claim 13, wherein the treated symptom of secondary hyperparathyroidism is elevated serum PTH and the elevated serum PTH is reduced to a serum level lower than about 300 pg/ml.

22. The method of claim 13, wherein the treated symptom of secondary hyperparathyroidism is elevated serum phosphorus.

23. The method of claim 13, wherein the treated symptom of secondary hyperparathyroidism is elevated serum creatinine.

24. The method of claim 13, wherein after treatment the subject has a serum calcium level within a range of 8.5-10.5 mg/dl.

* * * * *